(12) United States Patent
Funkhouser et al.

(10) Patent No.: US 7,549,320 B2
(45) Date of Patent: Jun. 23, 2009

(54) MEASURING CEMENT PROPERTIES

(75) Inventors: Gary Funkhouser, Duncan, OK (US);
Christian Meyer, Bergen, NJ (US);
David McMechan, Duncan, OK (US);
David Meadows, Marlow, OK (US);
Johnny Johnson, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 297 days.

(21) Appl. No.: 11/622,255

(22) Filed: Jan. 11, 2007

(65) Prior Publication Data

US 2008/0168848 A1 Jul. 17, 2008

(51) Int. Cl.
*G01M 3/02* (2006.01)
*G01N 17/00* (2006.01)

(52) U.S. Cl. ......................... 73/37; 73/865.6
(58) Field of Classification Search ............... 73/865.6, 73/37, 803
See application file for complete search history.

(56) References Cited

U.S. PATENT DOCUMENTS

| | | | |
|---|---|---|---|
| 2,662,827 A * | 12/1953 | Clark | ............ 106/720 |
| 3,574,281 A | 4/1971 | Casey et al. | |
| 3,619,463 A | 11/1971 | Budin et al. | |
| 3,779,085 A | 12/1973 | Rice | |
| 4,259,868 A | 4/1981 | Rao et al. | |
| 4,377,087 A | 3/1983 | Rodot | |
| 4,389,896 A | 6/1983 | Babcock | |
| 4,408,489 A | 10/1983 | Spangle | |
| 4,430,889 A | 2/1984 | Sutton | |
| 4,487,056 A | 12/1984 | Wiley | |
| 4,491,017 A | 1/1985 | Iyler | |
| 4,538,452 A | 9/1985 | Hrvojic | |
| 4,567,759 A | 2/1986 | Ekstrom et al. | |
| 4,567,765 A | 2/1986 | Rao et al. | |

(Continued)

FOREIGN PATENT DOCUMENTS

DE 86 01 833 1/1987

(Continued)

OTHER PUBLICATIONS

Foreign Communication related to a counterpart application dated Apr. 2, 2008.

(Continued)

*Primary Examiner*—Tung S Lau
*Assistant Examiner*—Nathaniel Kolb
(74) *Attorney, Agent, or Firm*—John W. Wustenberg; Fish & Richardson, P.C.

(57) ABSTRACT

A cement sample testing apparatus including a first pressure zone; a second pressure zone; and a pressure control system. The pressure control system can be in fluid communication with the first pressure zone and the second pressure zone, operable to raise the first pressure zone to a first pressure above ambient pressure, and operable to raise the second pressure zone to a second pressure above ambient pressure. A method for determining mechanical properties for a sample cement composition can include applying a first pressure condition to a first portion of the sample cement composition; applying a second pressure condition raised to a second portion of the sample cement composition; and determining one or more mechanical properties of the sample cement composition based at least in part on the pressure conditions present at the failure of the sample cement composition.

13 Claims, 4 Drawing Sheets

U.S. PATENT DOCUMENTS

| | | | |
|---|---|---|---|
| 4,607,530 A | 8/1986 | Chow | |
| 4,648,264 A * | 3/1987 | Freese et al. | 73/64.41 |
| 4,685,092 A | 8/1987 | Dumont | |
| 4,691,558 A | 9/1987 | Vinson et al. | |
| 4,703,427 A | 10/1987 | Catala et al. | |
| 4,757,479 A | 7/1988 | Masson et al. | |
| 4,809,237 A | 2/1989 | Vogel et al. | |
| 4,823,594 A | 4/1989 | Gray | |
| 4,848,145 A | 7/1989 | Blaschke et al. | |
| 4,893,285 A | 1/1990 | Masson et al. | |
| 4,896,303 A | 1/1990 | Leslie et al. | |
| 4,970,695 A | 11/1990 | Huau | |
| 5,009,512 A | 4/1991 | Lessi et al. | |
| 5,036,709 A | 8/1991 | McRae | |
| 5,089,989 A | 2/1992 | Schmidt et al. | |
| 5,127,473 A | 7/1992 | Harris et al. | |
| 5,216,638 A | 6/1993 | Wright | |
| 5,233,863 A | 8/1993 | Surjaatmadja et al. | |
| 5,248,200 A | 9/1993 | Walsh | |
| 5,325,723 A | 7/1994 | Meadows et al. | |
| 5,346,012 A | 9/1994 | Heathman et al. | |
| 5,353,637 A | 10/1994 | Plumb et al. | |
| 5,368,103 A | 11/1994 | Heathman et al. | |
| 5,377,160 A | 12/1994 | Tello et al. | |
| 5,377,753 A | 1/1995 | Haberman et al. | |
| 5,389,706 A | 2/1995 | Heathman et al. | |
| 5,412,990 A | 5/1995 | D'Angelo et al. | |
| 5,487,307 A | 1/1996 | Landgren et al. | |
| 5,488,994 A | 2/1996 | Laurel et al. | |
| 5,544,704 A | 8/1996 | Laurel et al. | |
| 5,571,951 A * | 11/1996 | Jamth | 73/54.03 |
| 5,572,021 A | 11/1996 | Heathman et al. | |
| 5,696,059 A | 12/1997 | Onan et al. | |
| 5,712,431 A | 1/1998 | Vilendrer | |
| 5,718,292 A | 2/1998 | Heathman et al. | |
| 5,741,971 A | 4/1998 | Lacy | |
| 5,763,773 A | 6/1998 | Birchak et al. | |
| 5,783,822 A | 7/1998 | Buchanan et al. | |
| 5,787,983 A | 8/1998 | Heathman et al. | |
| 5,836,200 A | 11/1998 | Belonenko et al. | |
| 5,869,750 A | 2/1999 | Onan et al. | |
| 5,964,293 A | 10/1999 | Chatterji et al. | |
| 5,968,255 A | 10/1999 | Mehta et al. | |
| 5,969,059 A | 10/1999 | Murai et al. | |
| 5,972,103 A | 10/1999 | Mehta et al. | |
| 5,992,223 A | 11/1999 | Sabins et al. | |
| 5,996,693 A | 12/1999 | Heathman | |
| 6,019,835 A | 2/2000 | Chatterji et al. | |
| 6,053,245 A | 4/2000 | Haberman | |
| 6,055,874 A | 5/2000 | Onan et al. | |
| 6,060,434 A | 5/2000 | Sweatman et al. | |
| 6,070,662 A | 6/2000 | Ciglenec et al. | |
| 6,112,599 A | 9/2000 | Maki, Jr. | |
| 6,124,246 A | 9/2000 | Heathman et al. | |
| H1932 H | 1/2001 | Heathman et al. | |
| 6,170,575 B1 | 1/2001 | Reddy et al. | |
| 6,209,646 B1 | 4/2001 | Reddy et al. | |
| 6,227,039 B1 | 5/2001 | Te'eni | |
| 6,227,294 B1 | 5/2001 | Chatterji et al. | |
| 6,245,142 B1 | 6/2001 | Reddy et al. | |
| 6,258,757 B1 | 7/2001 | Sweatman et al. | |
| 6,269,684 B1 | 8/2001 | Maki, Jr. et al. | |
| 6,270,565 B1 | 8/2001 | Heathman | |
| 6,345,535 B1 | 2/2002 | Sabins et al. | |
| 6,367,549 B1 | 4/2002 | Chatterji et al. | |
| 6,367,550 B1 | 4/2002 | Chatterji et al. | |
| 6,379,456 B1 | 4/2002 | Heathman et al. | |
| 6,444,316 B1 | 9/2002 | Reddy et al. | |
| 6,454,001 B1 | 9/2002 | Thompson et al. | |
| 6,478,868 B1 | 11/2002 | Reddy et al. | |
| 6,478,869 B2 | 11/2002 | Reddy et al. | |
| 6,484,568 B1 | 11/2002 | Griffith et al. | |
| 6,494,951 B1 | 12/2002 | Reddy et al. | |
| 6,527,051 B1 | 3/2003 | Reddy et al. | |
| 6,527,438 B2 | 3/2003 | Zollinger et al. | |
| 6,547,871 B2 | 4/2003 | Chatterji et al. | |
| 6,554,071 B1 | 4/2003 | Reddy et al. | |
| 6,591,910 B1 | 7/2003 | Chatterji et al. | |
| 6,595,068 B2 | 7/2003 | Brovold et al. | |
| 6,610,139 B2 | 8/2003 | Reddy et al. | |
| 6,644,402 B1 | 11/2003 | Sharma et al. | |
| 6,655,213 B1 | 12/2003 | Reinhardt et al. | |
| 6,660,080 B2 | 12/2003 | Reddy et al. | |
| 6,762,156 B2 | 7/2004 | Heathman et al. | |
| 6,767,867 B2 | 7/2004 | Chatterji et al. | |
| 6,782,735 B2 | 8/2004 | Walters et al. | |
| 6,789,621 B2 | 9/2004 | Wetzel et al. | |
| 6,797,054 B2 | 9/2004 | Chatterji et al. | |
| 6,817,238 B2 | 11/2004 | Go Boncan et al. | |
| 6,818,596 B1 | 11/2004 | Hayes | |
| 6,828,922 B1 | 12/2004 | Gremmert et al. | |
| 6,829,922 B2 | 12/2004 | Patin et al. | |
| 6,843,846 B2 | 1/2005 | Chatterji et al. | |
| 6,874,353 B2 | 4/2005 | Johnson et al. | |
| 6,892,814 B2 | 5/2005 | Heathman et al. | |
| 6,910,535 B2 | 6/2005 | Tare et al. | |
| 6,918,292 B2 | 7/2005 | Go Boncan et al. | |
| 6,951,249 B1 | 10/2005 | Chatterji et al. | |
| 6,964,302 B2 | 11/2005 | Luke et al. | |
| 6,978,835 B1 | 12/2005 | Reddy et al. | |
| 6,994,164 B2 | 2/2006 | Tare et al. | |
| 7,004,256 B1 | 2/2006 | Chatterji et al. | |
| 7,008,477 B2 | 3/2006 | Chatterji et al. | |
| 7,013,975 B2 | 3/2006 | Chatterji et al. | |
| 7,048,054 B2 | 5/2006 | Heathman et al. | |
| 7,089,816 B2 * | 8/2006 | Hakimuddin | 73/866 |
| 7,096,944 B2 | 8/2006 | Vargo, Jr. et al. | |
| 7,128,142 B2 | 10/2006 | Heathman et al. | |
| 7,128,149 B2 | 10/2006 | Heathman et al. | |
| 7,143,827 B2 | 12/2006 | Chatterji et al. | |
| 7,178,590 B2 | 2/2007 | Vargo, Jr. et al. | |
| 7,240,545 B1 | 7/2007 | Jennings | |
| 7,244,303 B2 | 7/2007 | Chatterji et al. | |
| 7,255,170 B2 | 8/2007 | Chatterji et al. | |
| 7,284,898 B2 | 10/2007 | Duell et al. | |
| 7,285,166 B2 | 10/2007 | Luke et al. | |
| 7,325,629 B2 | 2/2008 | Blaschke et al. | |
| 7,373,982 B2 | 5/2008 | Brothers et al. | |
| 7,380,466 B2 | 6/2008 | Deeg | |
| 2001/0001381 A1 | 5/2001 | Reddy et al. | |
| 2001/0037687 A1 | 11/2001 | Brovold | |
| 2003/0140707 A1 | 7/2003 | Pyle et al. | |
| 2003/0150263 A1 | 8/2003 | Economides et al. | |
| 2003/0161211 A1 | 8/2003 | Duell et al. | |
| 2003/0221829 A1 | 12/2003 | Patel et al. | |
| 2004/0054262 A1 | 3/2004 | Horak | |
| 2004/0055392 A1 | 3/2004 | Patin et al. | |
| 2004/0154263 A1 | 8/2004 | Li et al. | |
| 2004/0221990 A1 | 11/2004 | Heathman et al. | |
| 2004/0226483 A1 | 11/2004 | Chatterji et al. | |
| 2005/0009710 A1 | 1/2005 | Heathman et al. | |
| 2005/0080161 A1 | 4/2005 | Tare et al. | |
| 2005/0109507 A1 | 5/2005 | Heathman et al. | |
| 2005/0126300 A1 | 6/2005 | Go Boncan et al. | |
| 2005/0135185 A1 | 6/2005 | Duell et al. | |
| 2005/0152432 A1 * | 7/2005 | Hakimuddin | 374/53 |
| 2005/0204960 A1 | 9/2005 | Heathman et al. | |
| 2006/0000612 A1 | 1/2006 | Reddy et al. | |
| 2006/0225523 A1 * | 10/2006 | Reddy et al. | 73/865.6 |
| 2006/0258545 A1 | 11/2006 | Chatterji et al. | |
| 2007/0012441 A1 | 1/2007 | Heathman et al. | |
| 2007/0082822 A1 | 4/2007 | Kirsner et al. | |
| 2007/0105995 A1 | 5/2007 | Chatterji et al. | |
| 2007/0169937 A1 | 7/2007 | Allin et al. | |

| | | | |
|---|---|---|---|
| 2007/0173412 | A1 | 7/2007 | Allin et al. |
| 2008/0178683 | A1 | 7/2008 | Heathman et al. |
| 2008/0197605 | A1 | 8/2008 | Blaschke et al. |

FOREIGN PATENT DOCUMENTS

| | | |
|---|---|---|
| EP | 0 124 383 A1 | 11/1984 |
| EP | 0 176 400 B1 | 4/1986 |
| EP | 0 101 580 B1 | 12/1986 |
| EP | 0 110 750 B1 | 9/1988 |
| EP | 0 098 778 B1 | 3/1989 |
| EP | 0 198 985 B1 | 12/1989 |
| EP | 0 443 936 A1 | 2/1991 |
| EP | 0 443 936 A1 | 8/1991 |
| EP | 0 395 499 B1 | 7/1993 |
| EP | 0 176 408 B1 | 4/1996 |
| EP | 0 865 612 B1 | 6/2002 |
| EP | 1 541 987 | 6/2005 |
| GB | 2 353 546 A | 2/2001 |
| GB | 2 354 026 A | 3/2001 |
| GB | 2 355 742 A | 5/2001 |
| GB | 2 386 625 A | 9/2003 |
| WO | WO 00/49273 | 8/2000 |
| WO | WO 2004/008302 A1 | 10/2004 |
| WO | WO 2005/065411 | 7/2005 |

OTHER PUBLICATIONS

Bridgman, P. W., "V. Breaking Tests Under Hydrostatic Pressure and Conditions of Rupture", *Philosophical Magazine and Journal of Science*, vol. 24, Sixth Series, pp. 63-80, (1912).

Clayton, N., "Fluid-pressure Testing of Concrete Cylinders," *Magazine of Concrete Research*, vol. 30, No. 102, pp. 26-30, (1978).

Clayton, N., et al., "The Diphase Concept, With Particular Reference to Concrete", *Developments in Concrete Technology*, vol. 1, F. D. Lydon, Ed.; Applied Science Publisher Ltd, Chapter 7, pp. 283-318, (1979).

Deeg, Wolfgang et al., "How Foamed Cement Advantages Extend to Hydraulic Fracturing Operations," *World Oil*, pp. 51-53 (1999).

Dillenbeck, R. L. et al., "Testing Cement Static Tensile Behavior Under Downhole Conditions," SPE International, Society of Petroleum Engineers, SPE 97967, pp. 1-11, (2005).

FlexiForce®, materials downloaded from Tekscan website (www.tekscan.com) on FlexiForce® sensors), http://www.tekscan.com/flexiforce.html, visited Aug. 3, 2005, 20 pages.

Goodwin, K. J. et al., "Cement Sheath Stress Failure," *SPE Drilling Engineering*, SPE 20453, Dec. 1992, pp. 291-296, and additional pp. 501-508 from SPE 20453.

Love, A.E.H., "*A Treatise on the Mathematical Theory of Elasticity*," Fourth Edition, Dover Publications, New York, pp. 144-145, (1944).

Mindess, S. et al., "*The Nitrogen Gas Tension Test of Concrete*," Proceedings of ConMat '05 and Mindess Symposium, Aug. 22-24, 2005, The University of British Columbia, Vancouver, Canada, 8 pages, (2005).

Minear, John W. et al.,"Cement-Sheath Evaluation," *Petroleum Well Construction*, Chapter 10, pp. 271-296, (1998).

Richart, Frank E., et al., "A Study of the Failure of Concrete Under Combined Compressive Stresses", *The University of Illinois—Engineering Experiment Station*, Bulletin No. 185, pp. 3-253, (1928).

Thiercelin, M. J. et al., "Cement Design Based on Cement Mechanical Response," *SPE Drilling & Completion*, Society of Petroleum Engineers, SPE 52890, pp. 266-273 (1998).

International Search Report for PCT/GB2006/003052, mailed Dec. 21, 2006, 2 pages.

Office Action issued in related U.S. Appl. No. 11/669,771 on May 13, 2008 (14 pages).

Response to Office Action of May 13, 2008 filed on Aug. 13, 2008 in related U.S. Appl. No. 11/669,771 (10 pages).

Office Action issued in related U.S. Appl. No. 11/669,771 on Nov. 6, 2008 (10 pages).

Response to Office Action of Nov. 6, 2008 filed on Feb. 5, 2009 in related U.S. Appl. No. 11/669,771 (9 pages).

Final Office Action issued in related U.S. Appl. No. 11/669,771 on Mar. 11, 2009 (9 pages).

Office Action issued in related U.S. Appl. No. 11/622,255 on Jan. 2, 2009 (19 pages).

Office Action issued in related U.S. Appl. No. 11/206,719 on Jan. 24, 2008 (14 pages).

Response to Office Action of Jan. 24, 2008 filed on Feb. 21, 2008 in related U.S. Appl. No. 11/206,719 (10 pages).

Office Action issued in related U.S. Appl. No. 11/904,705 on Oct. 28, 2008 (11 pages).

Response to Office Action of Oct. 28, 2008 filed on Jan. 27, 2009 in related U.S. Appl. No. 11/904,705 (10 pages).

* cited by examiner

MEASURING CEMENT PROPERTIES

TECHNICAL FIELD

This invention relates to testing sample cement compositions, and more particularly to testing mechanical properties of sample cement compositions.

BACKGROUND

Some well bores, for example those of some oil and gas wells, are lined with a casing. The casing stabilizes the sides of the well bore, prevents fluids (liquids or gases) in the well bore from entering the surrounding earth formations, and/or prevents fluids from zones other than the producing zones from entering the well bore.

In a cementing operation, cement is introduced down the well bore and into an annular space between the casing and the surrounding earth. The cement secures the casing in the well bore, and prevents fluids from flowing vertically in the annulus between the casing and the surrounding earth.

Different cement formulations are designed for a variety of well bore conditions, which may be above ambient temperature and pressure. In designing a cement formulation, a number of potential mixtures may be evaluated to determine their mechanical properties under various conditions.

SUMMARY

In one aspect, cement sample testing apparatuses include: a first pressure zone; a second pressure zone; and a pressure control system in fluid communication with the first pressure zone and the second pressure zone, the pressure control system operable to raise the first pressure zone to a first pressure above ambient pressure and operable to raise the second pressure zone to a second pressure above ambient pressure.

In another aspect, cement sample testing apparatuses include: a pressure vessel having inner surfaces defining an interior cavity; a sample container disposed in the interior cavity of the pressure vessel; and first and second seal members disposed between the inner surfaces of the pressure vessel and the sample container, the first seal member divides a first section of the interior cavity from a second section of the interior cavity and the second seal member divides a third section of the interior cavity from the second section of the interior cavity such that the second section of the interior cavity is located between the first and third sections of the interior cavity.

In another aspect, methods for determining mechanical properties of a sample cement composition include: applying a first pressure condition changed from ambient conditions to a first portion of the sample cement composition; applying a second pressure condition changed from ambient conditions to a second portion of the sample cement composition, the second pressure condition being different than the first pressure condition; and determining one or more mechanical properties of the sample cement composition based at least in part on the pressure conditions present at the failure of the sample cement composition.

Embodiments of these apparatuses and methods can include one or more of the following features.

In some embodiments, the pressure control system is operable to raise the first pressure zone to a first pressure that is different than the second pressure. In some cases, the pressure control system comprises a first pump and a second pump.

In some embodiments, the first and second pressure zone are in fluid communication with each other.

In some embodiments, cement sample testing apparatuses can also include a pressure vessel and a seal adapted to isolate the first pressure zone from the second pressure zone. In some cases, the seal comprises an active seal switchable between a first configuration with a first inner diameter and a second configuration with a smaller inner diameter. In some cases, the pressure vessel includes a central port extending from an outer surface of the pressure vessel to the second section of the interior cavity of the pressure vessel and/or a first port extending from the outer surface of the pressure vessel to the first section of the interior cavity of the pressure vessel and a third port extending from the outer surface of the pressure vessel to the third section of the interior cavity of the pressure vessel. In some cases, a strain gauge is disposed in the interior cavity of the pressure vessel.

In some embodiments, cement sample testing apparatus can also include a third pressure zone.

In some embodiments, cement sample testing apparatus can also include a sample container. In some cases, the sample container comprises a portion transmissive to water and capable of containing a cement slurry.

In some embodiments, the first seal member and the second seal member each comprise an active seal switchable between a first configuration in which the active seal is spaced apart from the sample container and a second configuration in which the active seals engage the sample container.

In some embodiments, the sample container comprises: a first piston disposed in the interior cavity; a second piston disposed in the interior cavity, the second piston spaced apart from the first piston; and a sample sleeve extending between the first piston and the second piston. In some cases, cement sample testing apparatuses also include a spacer member disposed between an outer surface of one of the pistons and a corresponding inner surface of the pressure vessel. In some cases, cement sample testing apparatuses also include inserts disposed inside the sample container adjacent each piston, the inserts comprising a surface with a first friction coefficient that is lower than a second friction coefficient of the pistons.

In some embodiments, the sample container comprises a sleeve material transmissive to water and capable of containing a cement slurry. In some cases, the sleeve material comprises a micro-porous material (e.g., filter paper). In some cases, the sleeve material comprises a macro-porous material (e.g., perforated plastic).

In some embodiments, testing apparatuses also include a central cylinder disposed within and coaxially with the sample container.

In some embodiments, methods also include at least partially curing the sample cement composition at pressure conditions raised above ambient conditions.

In some embodiments, the first portion of the cement sample comprises a central portion of a cylindrical cement sample and the second portion of the cement sample comprises two spaced-apart end portions of the cylindrical cement sample separated by the central portion of the cylindrical cement sample. In some cases, applying the first pressure condition comprises increasing the first pressure condition until the cement sample fails. In some cases, applying the second pressure condition comprises increasing the second pressure condition until the cement sample fails.

In some embodiments, methods also include activating an active seal to isolate a first pressure zone from a second pressure zone.

Cement sample testing apparatuses and methods as described herein can be used to measure tensile strength, compressive strength, Young's modulus, Poisson's ratio, shrinkage and other properties. This versatility can reduce the number of testing devices necessary to perform comprehensive testing of a sample cement composition The details of one or more embodiments of the invention are set forth in the accompanying drawings and the description below. Other features, objects, and advantages of the invention will be apparent from the description and drawings, and from the claims.

DETAILED DESCRIPTION

The devices and methods described herein can allow an accurate measurement of mechanical properties and behaviors of cement formulations including, for example, tensile strength, compressive strength, shrinkage, and other properties. For example, a sample cement composition can be cured or partially cured at downhole conditions (e.g., temperatures and/or pressures elevated above ambient conditions) before differential pressures are applied to discrete portions of the cement sample (e.g., a first pressure is applied to one section of the cement sample and a second pressure that is different than the first pressure is applied to another section of the cement sample). Mechanical properties of the cement sample can be calculated based on the response of the sample to the differential pressures.

As used herein, "cement" and "cement composition" encompass a fluid mixture that hardens into solid, and may be any agent suitable to bond casing or other tubulars to well bore walls or to other tubing used for downhole applications. Some examples of cement include hydraulic cement (e.g., Portland cement formulations) and non-hydraulic cement (e.g., polymer resin formulations). As used herein, "curing" refers to the reactions through which cement hardens from a fluid mixture into a solid. In some instances, the devices and methods discussed herein can be used to measure mechanical properties at temperatures and pressures that simulate downhole conditions.

Figure 1:
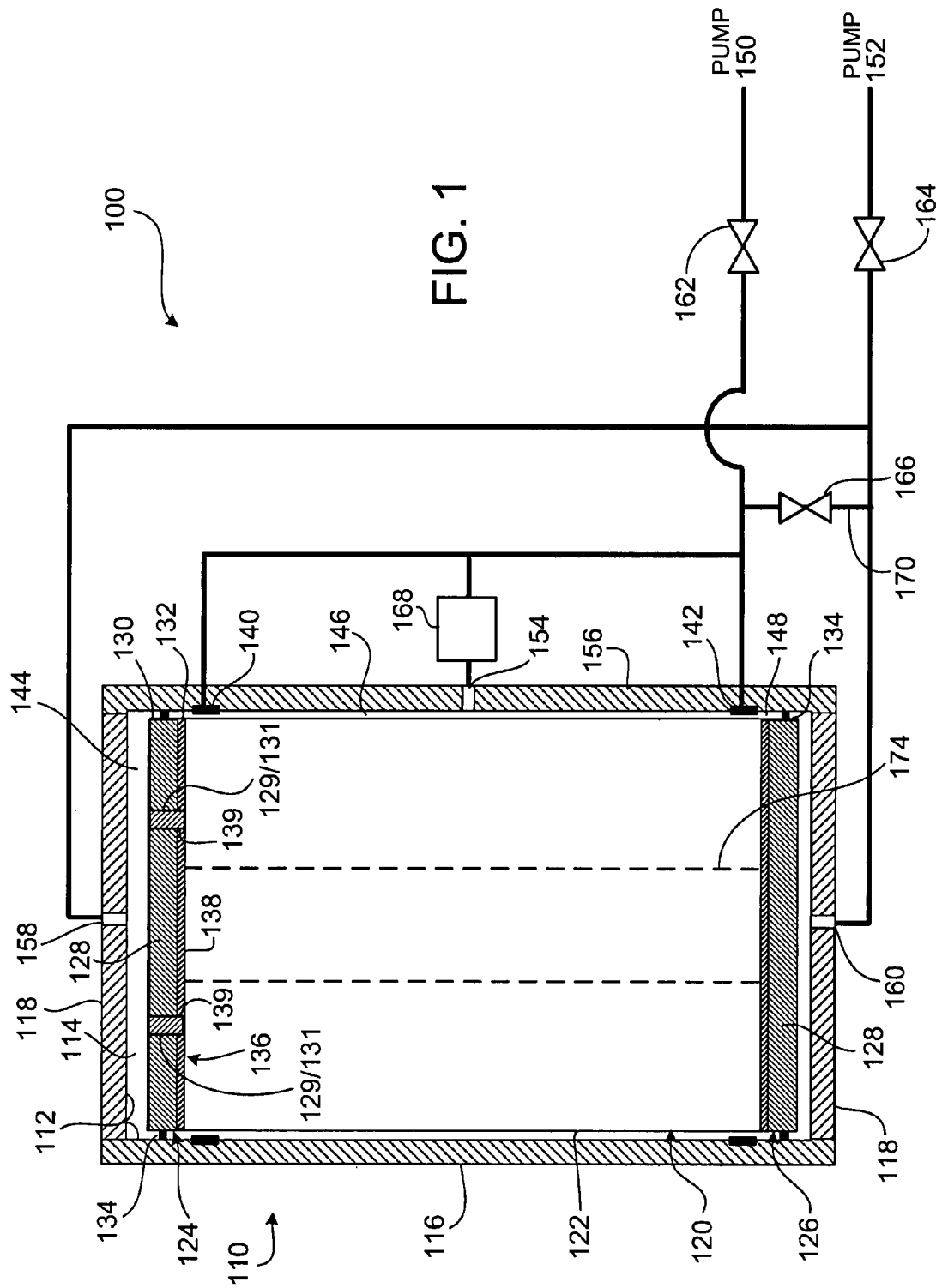
FIG. 1 is a schematic view of an embodiment of a cement testing apparatus.

Referring to FIG. 1, an example cement sample testing apparatus 100 includes a pressure vessel 110 having inner surfaces 112 defining an interior cavity 114. In some instances, pressure vessel 110 includes a hollow cylindrical body 116 and end caps 118. The end caps 118 are attached to the cylindrical body 116 to form a pressure tight seal. For example, the end caps 118 can be threaded or otherwise fastened to the cylindrical body 116. A seal or seals (e.g., o-rings) can be provided to enhance the pressure-tight fit between the cylindrical body 116 and the end caps 118. In some cases, the cylindrical body 116 and end caps 118 are made of steel or other suitable materials. In some embodiments, the pressure vessel 110 can be configured with other (e.g., non-cylindrical) shapes.

A sample container 120 is disposed in the interior cavity 114 of the pressure vessel 110. Sample container 120 has portions including (e.g., formed of) metallic, plastic, or other suitable material operable to communicate changes of pressure to a cement sample in the sample container 120. For example, the sample container 120 can include a first piston 124, a second piston 126 spaced apart from the first piston 124; and a sample sleeve or sidewalls 122 extending between the first piston 124 and the second piston 126. Sidewalls 122 can be formed of metallic, plastic, or other suitable material operable to communicate changes of pressure to a cement sample in the sample container 120.

The pistons 124, 126 can include a plate 128 having an outer surface 130 that is configured to match a corresponding portion 132 of the inner surfaces 112 of the pressure vessel 110. Plates can be sized and configured such that the outer surface 130 of each plate 128 has a first perimeter that is smaller than a second perimeter of the corresponding inner surface 132 of the pressure vessel 110 (e.g., the plate 128 fits within the pressure vessel 110). Upper plate 128 can include two fill holes 129 that can be sealed with associated plugs 131. Plates 128 can include (e.g., are made of) steel or other suitable materials.

In some embodiments, sidewalls 122 are formed of metallic, plastic, or other suitable material(s) (e.g., rubber, filter paper, brass, or aluminum) operable to communicate changes of pressure to a cement sample in the sample container 120. In addition, the material used for the sidewalls 122 is capable of containing a cement slurry. For example, a material transmissive to water and capable of containing a cement slurry can be used to form the sidewalls 122. In some cases, the sidewalls 122 include a micro-porous material. As used herein, micro-porous materials are materials whose internal structure contains sufficient interconnected void spaces to allow for the transmission of fluids such as water or nitrogen gas through the material. For example, filter paper would be considered a micro-porous material. In some cases, sidewalls 122 include a macro-porous material. As used herein, macro-porous materials are materials in which discrete bores extend directly through the material from one side of the material to an opposite side of the material. Macro-porous materials may also have micro-porous characteristics (e.g., filter paper that has been needled to form discrete holes extending through the filter paper) or may have an internal structure substantially impervious to fluids (e.g., a perforated Kapton® film). By attaching sidewalls 122 to circular pistons 124, 126, cylindrical sample container 120 can be formed.

The sample container 120 can have sufficient structural stability to hold a cement slurry in a desired shape while it cures. For example, a thin rubber sleeve can be stiffened with closely spaced o-rings or a thin rubber sleeve can be stiffened with an o-ring glued on the outside of the sleeve in a spiral pattern or a thicker rubber sleeve can be used.

In some instances, spacers can be installed between the plates 128 and the pressure vessel 110 to maintain the relative spacing position between the plates 128 and the interior surfaces of the pressure vessel 110. For example, the pistons 124, 126 can include a spacer member 134 disposed between the outer surface 130 of the plate and the corresponding inner surface 132 of the pressure vessel 110. Spacer members 134 help maintain a desired position of the sample container 120 relative to the inner surfaces 112 of the pressure vessel 110. Spacer members 134 can be o-rings arranged to provide a small but discrete distance (e.g., 0.001 inch, 0.005 inch, or 0.01 inch) between the sample sleeve 122 and interior surface 132 of the body 116 of the pressure vessel 110.

Some cement sample testing apparatuses include low friction inserts located adjacent to the plates to limit bonding between the pistons and the cement composition being tested. For example, cement sample testing apparatus 100 includes inserts 136 disposed inside the sample container 120 adjacent each plate 128. The inserts 136 include (e.g., are made of and/or are layered with) a material having a low coefficient of friction (e.g., less than about 0.2, 0.1, 0.05, or 0.025). In some embodiments, inserts 136 can be thin stainless steel plates coated with Teflon® or other suitable materials. This provides inserts 136 with a surface 138 having a first friction coefficient that is lower than a second friction coefficient of the plates. Top insert 136 includes two fill holes 139 whose locations match the locations of the fill holes extending through the top plate 128.

In order to enable application of differential pressures to a sample being tested, some cement testing apparatuses can also include seals dividing the interior cavity into multiple pressure-tight sections. As the seals are used during testing, the seals are configured to cooperate with the sample container and sample cement composition in forming the multiple pressure-tight sections. For example, seals extending between interior walls of a pressure vessel to engage a sample container and sample cement composition can form multiple pressure-tight sections that would be in fluid communication in the absence of the sample container and sample cement composition. The seals can be active seals (e.g., seals that are pressurized to switch from an inactive first configuration to an active second configuration with a smaller inner diameter) that are activated after the sample cement composition is at least partially cured or passive seals. Thus, the term dividing is used broadly to indicate seals disposed at the interface between discrete sections of a pressure vessel whether or not the seals limit fluid communication between the sections of the pressure vessel in all configurations and/or in the absence of a sample container and sample cement composition.

For example, referring again to FIG. 1, cement testing apparatus 100 includes a first seal member 140 and a second seal member 142 that are disposed adjacent to inner surfaces 112 of pressure vessel 110 such that the seal members 140, 142 are between the inner surfaces of the pressure vessel 110 and the sample container 120 when the sample container is placed in pressure vessel 110 for testing a sample cement composition. The first seal member 140 divides a first section 144 of the interior cavity 114 from a second section 146 of the interior cavity 114 and the second seal member 142 divides a third section 148 of the interior cavity 114 from the second section 146 of the interior cavity 114 such that the second section 146 of the interior cavity 114 is located between the first and third sections 144, 148 of the interior cavity 114.

In some embodiments, including the illustrated embodiment, the first and second seal 140,142 are active seals which are switchable between a first configuration (shown in FIG. 1) in which the active seal is spaced apart from the sample container 120 and a second configuration (not shown) in which the active seals engage the sample container 120. Thus, when the seals 140, 142 are in their first configuration, the first, second, and third sections 144, 146, 148 of the interior cavity are in fluid communication with each other. When sample container 120 containing a sample cement composition is inserted and seals 140, 142 are activated to engage the sample container 120 and sample cement composition, the first, second, and third sections 144, 146, 148 of the interior cavity 114 can be isolated from each other such that differential pressures can be applied to individual sections as described in more detail below. Pressure applied by first pump 150 can activate seals 140, 142. In this embodiment, spacer members 134 have apertures extending therethrough which provide fluid communication between opposite sides of the spacer members 134.

Cement testing apparatuses can also include ports extending through the pressure vessel into the multiple sections of their interior cavities. For example, referring again to FIG. 1, cement testing apparatus 100 includes a central port 154 extending from an outer surface 156 of the pressure vessel 110 to the second section 146 of the interior cavity 114 of the pressure vessel 110. Cement testing apparatus 100 also includes a first port 158 extending from an outer surface 156 of the pressure vessel 110 to the first section 144 of the interior cavity 114 of the pressure vessel 110 and a third port 160 extending from the outer surface of the pressure vessel 110 to the third section 148 of the interior cavity 114 of the pressure vessel 110.

First and second pumps 150, 152 and associated piping are used to independently control pressure conditions in the multiple sections 144, 146, 148 of the interior cavity 114 of the pressure vessel 110. First valve 162 and second valve 164 are interposed between first pump 150 and second pump 152, respectively, and the remainder of the associated piping system. Isolation valve 166 is disposed on interconnect piping 170 that can provide fluid communication between the portions of the piping connected to central port 154 and the portions of the piping connected to first and second ports 158, 160. Pressure relief valve 168 is disposed on the piping directly connected to central port 154 and allows engagement of the active seals 140, 142 before opening flow to the second section 146 of the cell. Other arrangements of pumps, valves, and piping can also be used to apply differential pressures to discrete sections of the interior cavity 114 of the pressure vessel 110. Similarly, other pressure control systems (e.g., pressure control systems using pressurized gas cylinders rather than pumps) can be used.

Cement sample testing apparatuses can include sensors to measure parameters used to calculate properties of cement samples being tested. For example, cement sample testing apparatus 100 may include linear variable displacement transducers (LVDTs) positioned at 120 degree intervals around a circle between upper steel plate 128 and end cap 118 or in other suitable positions. The average reading of the three LVDTs can be used to characterize the length change of the sample during testing. Other sensors, such as strain gauges, can be used in addition to or in place of the LVDTs to measure relevant parameters. For example, four strain gauges (two vertical and two tangential) could be attached to interior surfaces of a rubber sleeve to provide material data that would be difficult to obtain otherwise. Alternatively, strain gauges could be attached to exterior surfaces of an aluminum sleeve. Similarly, the amount of fluid (e.g., water) pumped into the pressure vessel 110 as the cement cures can provide a measure of cement shrinkage. Pressure sensors can be included to measure pressures present during testing.

Temperature can be controlled to simulate downhole conditions. The cement testing apparatus 100 and cement slurry can be preheated during mixing. The desired temperature can be maintained as the sample cement composition cures using external heating elements (e.g., heater coils or stainless steel heater bands) or placing the cement testing apparatus 100 in an oven.

Figure 2:
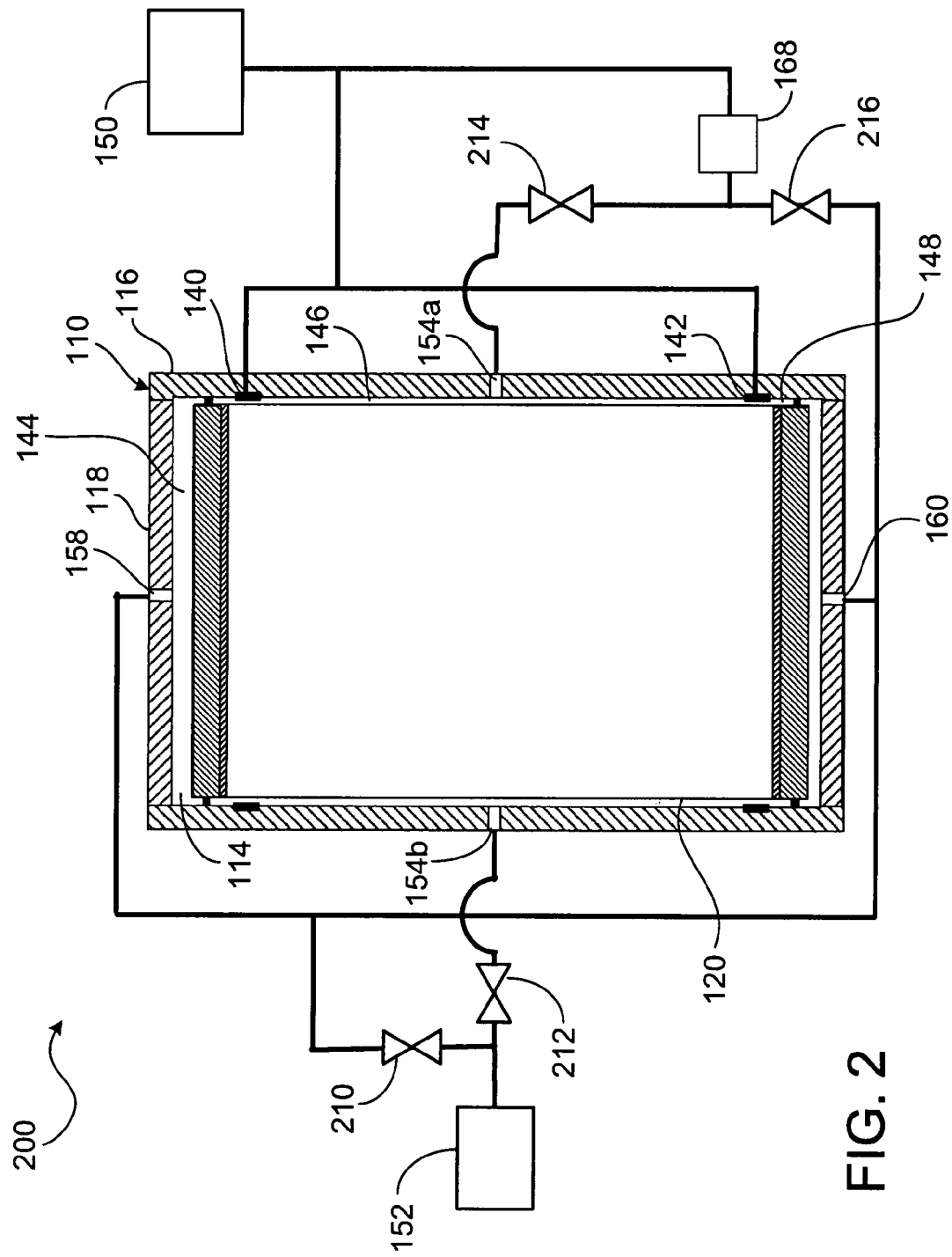
FIG. 2 is a schematic view of another embodiment of a cement testing apparatus.

Referring to FIG. 2, another example cement sample testing apparatus 200 is configured to enable a single testing apparatus to be used to perform both compressive and tensile strength tests. Cement sample testing apparatus 200 is substantially similar to cement testing apparatus 100 but includes an alternate arrangement of pumps, valves, and piping to apply differential pressures to discrete sections of the interior cavity 114 of the pressure vessel 110.

Cement sample testing apparatus 200 includes a pressure vessel 110 with a hollow body 116 and end caps 118. The end caps 118 are attached to the body 116 to form a pressure tight seal. The sample container 120 is disposed in the pressure vessel 110. Active seals 140, 142 can isolate the first, second, and third sections 144, 146, 148 of interior cavity 114 from each other when sample container 120 is present. First port 158, central ports 154a, 154b, and third port 160 extend through the pressure vessel 110 to the interior cavity 114 of the pressure vessel 110.

First and second pumps 150, 152 and associated piping are used to independently control pressure conditions in the multiple sections 144, 146, 148 of the interior cavity 114 of the pressure vessel 110. As in cement sample testing apparatus 100, pressure relief valve 168 is disposed on the piping connected to central port 154a and allows engagement of the active seals 140, 142 before opening flow to the interior cavity 114 of the cell. Flow paths from the first and second pumps 150, 152 can each be connected various combinations of the ports 154, 158, 160 based on the settings of valves 210, 212, 214, 216 as required for a particular test.

For example, when performing a tensile strength test, valve 210 and valve 214 can be opened and valve 212 and valve 216 can be closed. After a sample cement composition is placed in sample container 120, pump 152 can be used to set the pressure in the pressure vessel 110 at which the sample cement composition will be cured by supplying pressurizing fluid to the first port 158 and the third port 160. At this point, the active seals 140, 142 are in their inactive state. After curing to the extent desired, the pump 150 can be operated to supply pressurizing fluid to the active seals 140, 142 and, since valve 214 is open and valve 216 is closed, to the central port 154a. Applying pressure to the active seals 140, 142 activates them to isolate first, second, and third sections 144, 146, 148 of the interior cavity 114 from each other. Pump 150 can be used to apply increasing pressure to the second section 146 via port 154a until the sample fails.

In another example, when performing a compressive strength test, valve 210 and valve 214 can be closed and valve 212 and valve 216 can be opened. After a sample cement composition is placed in sample container 120, pump 152 can be used to set the pressure in the pressure vessel 110 at which the sample cement composition will be cured by supplying pressurizing fluid to the central port 154b. At this point, the active seals 140, 142 are in their inactive state. After curing to the extent desired, the pump 150 can be operated to supply pressurizing fluid to the active seals 140, 142 and, since valve 214 is closed and valve 216 is opened, to the first port 158 and the third port 160. Applying pressure to the active seals 140, 142 activates them to isolate first, second, and third sections 144, 146, 148 of the interior cavity 114 from each other. Pump 150 can be used to apply increasing pressure to the first and third section 144, 148 via the first and third ports 158, 160 until the sample fails.

Methods of determining properties of a sample cement composition can be performed using testing apparatuses to apply differential pressures on different portions of a cement sample. A sample container can be placed in the interior cavity of a pressure vessel before the sample container is filled with a sample cement composition to be tested. The sample cement composition can be cured or partially cured inside the pressure vessel at temperatures and/or pressures that simulate downhole conditions. Seals can separate multiple sections of the interior cavity of the pressure vessel from each other. A first pressure can be applied in one section and a different pressure can be applied in another section. Differential pressures can be applied to different portions of the sample cement composition being tested until the sample cement composition fails. Mechanical properties of the sample cement composition can be calculated based, at least in part, on conditions and properties associated with the pressure vessel and the sample cement composition as the differential pressure is applied.

Figure 3:
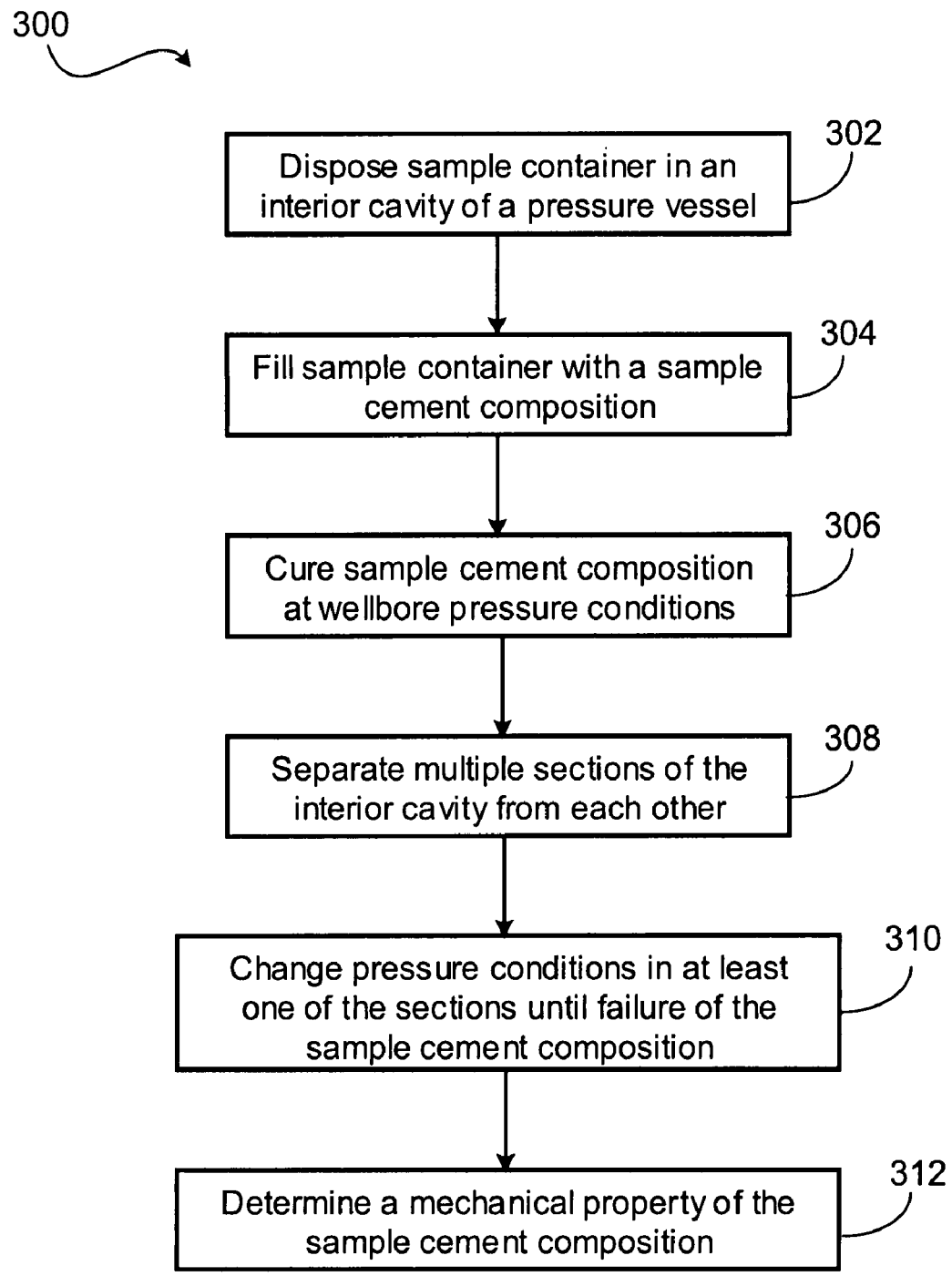
FIG. 3 is a flowchart of an embodiment of cement testing method.

Referring to FIG. 3, an example method 300 can include disposing a sample container 120 in an interior cavity 114 of a pressure vessel (step 302). For example, a rubber sleeve can be glued to two circular steel plates (one at the top of the rubber sleeve and the other at the bottom of the rubber sleeve) to form a cylindrical sample container. The top steel plate can have multiple holes extending therethrough to be used in filling the sample container. For example, the top steel plate can have two holes spaced apart from each other along a single diameter of the top steel plate at equal distances from the center of the plate. In some cases, there may be more than two holes and/or the locations of the holes may be varied (e.g., the top steel plate may be tapered, getting thinner toward the center where it has a hole, with the second hole somewhere else on the plate).

The sample container can be filled with a sample cement composition (step 304). For example, a cement slurry can be added to (e.g., pumped into or poured into) the sample container through a first hole while air and water escape from the sample container through a second hole. When slurry escapes through the second hole, the entire sample container is filled with slurry. Other ways of filling the sample container are also possible (e.g., using a syringe to fill a sample container from the bottom to the top). After the sample container is filled with slurry, the holes can be plugged. The sample container can be filled and then placed in the pressure vessel or the sample container can be placed in the pressure vessel and then filled.

The sample cement composition can be cured within the interior cavity of the pressure vessel at specified pressures and temperatures (step 306). The specified pressures and temperatures can be chosen to simulate well bore pressure and/or temperature conditions or other pressure and/or temperature conditions under which a cement sample's properties are of interest. Simulated downhole pressure and temperature conditions can be actual downhole conditions (e.g., 350 degrees Fahrenheit and 15,000 psi) or modified conditions. The pressure vessel can be heated using a thermal blanket or through the application and/or circulation of a heated fluid (e.g., water) to interior portions of the pressure vessel, with the temperature being controlled by internal thermocouples. A pressurizing fluid (e.g., water or a gas such as nitrogen) can be pumped into the pressure vessel through ports extending through the walls of the pressure vessel. Water is inexpensive, can be safer to use than pressurized gases, and simplifies associated logistics. By controlling the temperature and/or pressure present while the sample cement composition cures, the properties of the sample cement composition measured during testing closely reflect the properties of similar cement compositions during actual use.

Seals can be used to separate sections of the interior cavity from each other (step 308). For example, a first seal member disposed between an inner surface of the pressure vessel and the sample container can separate a first section of the interior cavity from a second section of the interior cavity and a second seal member disposed between the inner surface of the pressure vessel and the sample container can separate a third section of the interior cavity from the second section of the interior cavity such that the second section of the interior cavity is located between the first and third sections of the interior cavity.

In some cases, the seals are active seals and using the first seal member and using the second seal member can include activating the active seals to engage the sample container after the sample cement composition has at least partially cured.

Pressure can be applied to activate the seals independently of the application of differential pressure to the separate section. Alternatively, pressure can be applied to activate the seals in conjunction with the application of the differential pressures (e.g., conduits in fluid communication with each can be used to supply pressurizing fluid to both the second section of the interior cavity and to active seals that separate the second section from the first and third sections). By using active seals, the sample cement composition can be allowed to cure before the seals engage the sample container in the sample cement composition contained within. This can avoid indentations in the sample cement composition that can result if seals engage sample cement composition before it cures. It is advantageous to avoid such indentations because they can be an anomalous point of weakness in the sample whose early failure can distort the calculation of the properties being measured.

After the sections of the interior cavity are separated from each other, pressure conditions in at least one of the sections can be changed to induce failure of the cured sample cement composition (step 310). For example, pressure conditions can be changed in at least one of the first, second, and third sections of the pressure vessel until the failure of the cured sample cement composition. In some cases, changing pressure conditions comprises increasing pressure conditions in the second section of the interior cavity (e.g., by pumping water into the second section of the interior cavity through a central port extending from an outer surface of the pressure vessel to the second section of the interior cavity of the pressure vessel). In some cases, changing pressure conditions comprises increasing pressure conditions in the first and third sections of the interior cavity of the pressure vessel (e.g., by pumping water into the first and third sections of the interior cavity through a first port extending from an outer surface of the pressure vessel into the first section the interior cavity of the pressure vessel and through a third port extending from an outer surface of the pressure vessel to the third section of the interior cavity of the pressure vessel). Failure of the cement sample can be indicated, for example, by a rapid change in LVDT readings, by a large increase in water needed to maintain pressure in a section of the pressure vessel, and/or by water being expelled from another section of the pressure vessel.

Based at least in part on pressure conditions in at least one of the first, second, and third sections of the pressure vessel, one or more mechanical properties of the sample cement composition can be determined (step 312).

The tensile strength of a sample cement composition can be determined (e.g., precisely determined or estimated) by applying increasing levels of fluid pressure to a central portion of a cylindrical cement sample while the end of portions of the cylindrical cement sample remain in a baseline pressure (e.g., atmospheric pressure or pressure consistent with downhole conditions). The fluid pressure at failure may be equal or proportional to the tensile strength of the cement composition. During such testing, the sample cement composition's change in length can be measured (e.g., using LVDTs) to provide a basis for calculating Young's modulus using standard methods. In some embodiments, cement shrinkage during curing can be measured by recording the volume of water pumped into the testing apparatus to maintain a constant pressure during curing.

A sample cement composition can also be tested under compression. For example, pressures can be increased in the first and third sections of a three-section testing apparatus until failure of the sample cement specimen. To perform compression testing, the cement testing apparatus can be configured with sufficient space between the exterior walls of the sample container and the interior walls of the pressure vessel to allow for the cement composition being tested to expand laterally due to Poission's ratio effect. For example, a 2 inch by 4 inch cement specimen with a Young's modulus of 3000 ksi and a Poisson's ratio of 0.2 should fail at a vertical strain of about 0.002 and a horizontal strain of about 0.0004. At this point, the specimen's radius should have increased by about 0.0004 inch and at least this much gap must be provided between the sample container and the pressure vessel.

Using this method, multiple tests can be conducted in parallel using a single set of pumps. For example, the pumps can be used to pressurize multiple pressure vessels with each pressure vessel sealed and set aside for the cement to cure while other pressure vessels are being filled or tested. After the various cement specimens have reached the desired stage of curing, they can be tested to failure one at a time with the two pumps.

The following example is intended to illustrate the benefits of the present invention, but does not exemplify the full scope of the invention. Thus, this example does not limit the claimed invention.

Figure 4:
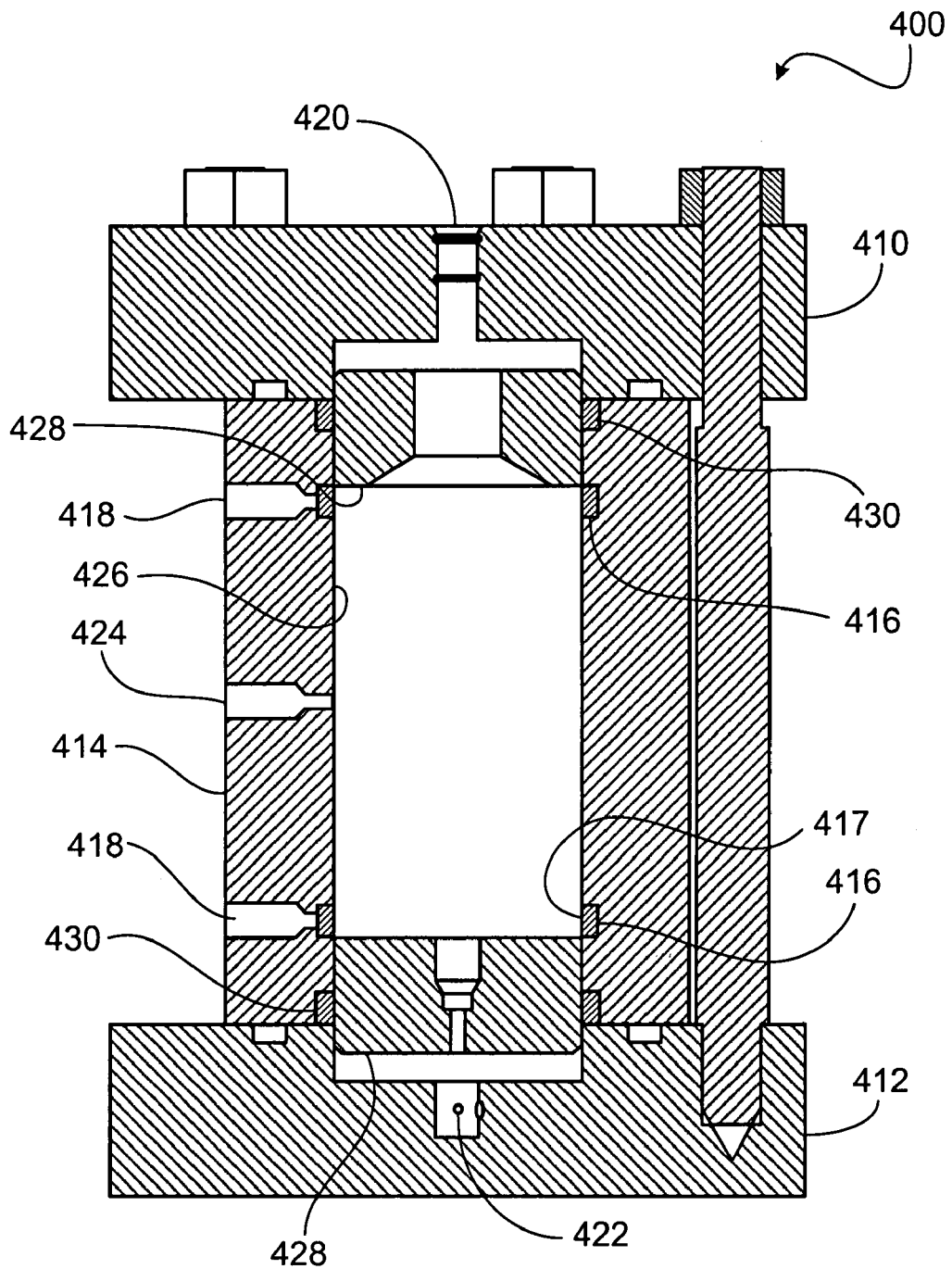
FIG. 4 is a cross-sectional view of an embodiment of test cell. Like reference symbols in the various drawings indicate like elements.

Referring to FIG. 4, a tension cell assembly was used as the pressure test cell 400. Pressure test cell 400 included a top 410, a bottom 412, and a cylinder 414. Grooves 416 (0.275 inch wide and 0.12 inch deep) were cut into the interior surface of the cylinder 414 0.764 inch from each end of the pressure test cell 400. Rubber rings 417 (approximately 0.27 inch wide, 2.15 inches inner diameter, 0.12 inch thick) were installed in the grooves 416 to complete the active seal. An eighth inch national pipe thread (NPT) port 418 extended through the cylinder 414 of the pressure test cell 400 into each groove 416 to pressurize the seal. Three additional ports 420, 422, 424 extended through the wall of the pressure test cell—one port 420, 422 at each end and one port 424 between the active seals.

A 5 inches by 8.5 inches piece of 3-mil Kapton® film 426 was perforated approximately 100 times with a syringe needle. The sealing surfaces of the film 426 were roughened with 325 grit sandpaper, rinsed with isopropyl alcohol, and air dried. The film 426 was glued around two pistons 428 with Loctite® Black Max adhesive to form a cylindrical sample container. The sample container was installed in the pressure test cell 400 with O-rings 430 inserted adjacent each piston 428 to hold the sample container in place. Each O-ring 430 had a segment approximately an eighth of an inch in length removed to allow fluid flow past the O-ring 430.

A cement slurry was prepared by mixing 600 grams of Class A cement, 12 grams anhydrous calcium chloride, and 276 grams of tap water in a Waring® blender at 12,000 RPMs for 35 seconds. The sample container was filled with the cement slurry before the ends 410, 412 of the pressure test cell were bolted into place.

A cell end manifold included conduits connected to the top and bottom ports 420, 422. An active seal/annulus manifold included conduits connected to both active seal ports 418 and to a pressure relief valve attached to the port 424 between the active seals. Interconnect piping joining the two manifolds included an isolation valve enabling isolation of the manifolds from each other. A first syringe pump was connected to the cell end manifold and a second syringe pump was connected to the active seal/annulus manifold.

After purging air from the system with water, the pressure was increased to 1000 psi by setting the first syringe pump to maintain a constant 1000 psi pressure with the isolation valve open.

The sample was allowed to cure for 24 hours at ambient temperature. After 24 hours, the isolation valve was closed before the second syringe pump was brought up to 1000 psi and opened to the active seal/annulus manifold. The second syringe pump was then set to provide a constant water flow rate of 2 milliliters per minute. The annular pressure increased to a maximum differential pressure of 657 psi relative to the pressure maintained by the first syringe pump on the ends of the cement sample (i.e., a total pressure of 1657 psi) before suddenly dropping as the cement sample failed. Upon removing the sample from the apparatus, the cement sample was found to have a clean transverse break approximately one quarter of the way down from the top of the sample.

A number of embodiments of the invention have been described. Nevertheless, it will be understood that various modifications may be made without departing from the spirit and scope of the invention. For example, the illustrated cement sample testing apparatus includes two seals which divide the interior cavity of the pressure vessel into three discrete sections. Some embodiments include more seals (e.g., three seals) which divide the interior cavity of the pressure vessel into more discrete sections(e.g., four sections). Accordingly, other embodiments are within the scope of the following claims.

What is claimed is:

1. A cement sample testing apparatus, comprising:
   a first pressure zone;
   a second pressure zone;
   a pressure control system in fluid communication with the first pressure zone and the second pressure zone, the pressure control system operable to raise the first pressure zone to a first pressure above ambient pressure and operable to raise the second pressure zone to a second pressure above ambient pressure;
   a pressure vessel and a seal adapted to isolate the first pressure zone from the second pressure zone, wherein the seal comprises an active seal switchable between a first configuration with a first inner diameter and a second configuration with a smaller inner diameter.

2. The apparatus of claim 1, wherein the pressure control system is operable to raise the first pressure zone to a first pressure that is different than the second pressure.

3. The apparatus of claim 1, wherein the first and second pressure zone are in fluid communication with each other.

4. The apparatus of claim 1, further comprising a third pressure zone.

5. The apparatus of claim 1, further comprising a sample container.

6. The apparatus of claim 5, wherein the sample container comprises a portion transmissive to water and capable of containing a cement slurry.

7. The apparatus of claim 1, wherein the pressure control system comprises a first pump and a second pump.

8. A cement sample testing apparatus comprising:
   a pressure vessel having inner surfaces defining an interior cavity;
   a sample container disposed in the interior cavity of the pressure vessel; and
   first and second seal members disposed between the inner surfaces of the pressure vessel and the sample container, the first seal member divides a first section of the interior cavity from a second section of the interior cavity and the second seal member divides a third section of the interior cavity from the second section of the interior cavity such that the second section of the interior cavity is located between the first and third sections of the interior cavity.

9. The apparatus of claim 8, wherein the first seal member and the second seal member each comprise an active seal switchable between a first configuration in which the active seal is spaced apart from the sample container and a second configuration in which the active seals engage the sample container.

10. The apparatus of claim 8, wherein the sample container comprises:
    a first piston disposed in the interior cavity;
    a second piston disposed in the interior cavity, the second piston spaced apart from the first piston; and
    a sample sleeve extending between the first piston and the second piston.

11. The apparatus of claim 10, further comprising a spacer member disposed between an outer surface of one of the pistons and a corresponding inner surface of the pressure vessel.

12. The apparatus of claim 10, further comprising inserts disposed inside the sample container adjacent each piston, the inserts comprising a surface with a first friction coefficient that is lower than a second friction coefficient of the pistons.

13. The apparatus of claim 8, wherein the sample container comprises a sleeve material transmissive to water and capable of containing a cement slurry.

* * * * *